(12) United States Patent
Ogawa et al.

(10) Patent No.: US 10,136,643 B2
(45) Date of Patent: Nov. 27, 2018

(54) FUNGICIDAL COMPOSITION AND METHOD FOR CONTROLLING PLANT DISEASES

(71) Applicant: ISHIHARA SANGYO KAISHA, LTD., Osaka-shi (JP)

(72) Inventors: Munekazu Ogawa, Kusatsu (JP); Akihiro Nishimura, Kusatsu (JP)

(73) Assignee: ISHIHARA SANGYO KAISHA, LTD., Osaka-shi (JP)

(*) Notice: Subject to any disclaimer, the term of this patent is extended or adjusted under 35 U.S.C. 154(b) by 0 days.

(21) Appl. No.: 15/237,194

(22) Filed: Aug. 15, 2016

(65) Prior Publication Data
US 2016/0353737 A1    Dec. 8, 2016

Related U.S. Application Data

(62) Division of application No. 14/572,237, filed on Dec. 16, 2014, now Pat. No. 9,474,281, which is a division of application No. 13/002,361, filed as application No. PCT/JP2009/062259 on Jun. 30, 2009, now Pat. No. 8,962,661.

(30) Foreign Application Priority Data

Jul. 3, 2008 (JP) .................... 2008-174963
Nov. 14, 2008 (JP) .................... 2008-292511

(51) Int. Cl.
| | |
|---|---|
| *A01N 43/40* | (2006.01) |
| *A01N 37/06* | (2006.01) |
| *A01N 43/42* | (2006.01) |
| *A01N 43/56* | (2006.01) |
| *A01N 43/78* | (2006.01) |
| *A01N 43/90* | (2006.01) |
| *A01N 59/02* | (2006.01) |
| *A01N 37/48* | (2006.01) |
| *A01N 47/12* | (2006.01) |
| *A01N 47/24* | (2006.01) |
| *A01N 43/653* | (2006.01) |

(52) U.S. Cl.
CPC ............ *A01N 43/40* (2013.01); *A01N 37/48* (2013.01); *A01N 43/42* (2013.01); *A01N 43/56* (2013.01); *A01N 43/653* (2013.01); *A01N 43/78* (2013.01); *A01N 43/90* (2013.01); *A01N 47/12* (2013.01); *A01N 47/24* (2013.01); *A01N 59/02* (2013.01)

(58) Field of Classification Search
CPC combination set(s) only.
See application file for complete search history.

(56) References Cited

U.S. PATENT DOCUMENTS

| | | |
|---|---|---|
| 2006/0194849 A1 | 8/2006 | Nishide et al. |
| 2009/0247763 A1 | 10/2009 | Nishide et al. |

FOREIGN PATENT DOCUMENTS

| | | | |
|---|---|---|---|
| EP | 1 679 003 | 7/2006 | |
| EP | 2036436 A1 * | 1/2008 | ............ A01N 43/40 |
| JP | 2004-35435 | 2/2004 | |
| JP | 2006-52195 | 2/2006 | |
| WO | WO 98/46607 | 10/1998 | |
| WO | WO 98/55460 | 12/1998 | |
| WO | WO02 02527 | 1/2002 | |
| WO | WO-2008004596 A1 * | 1/2008 | ............ A01N 43/40 |
| WO | WO 2008/061655 A2 | 5/2008 | |
| WO | WO 2008/101976 A1 | 8/2008 | |

OTHER PUBLICATIONS

Endura fungicide label, BASF Chemical Company, pp. 1-27 and supplemental label pp. 1-5 (Jun. 18, 2008).*
Leonard, P.K., "Resistance risk evaluation, 'A European regulatory perspective,'" Crop Protection, vol. 19, pp. 905-909 (2000).*
Issac, S., "What is the mode of action of fungicides and how do fungi develop resistance?" Mycologist, vol. 13(1), pp. 38-39 (1999).*
Bartlett, D.W., et al., "Review: The strobiluring fungicides," Pest Management Science, vol. 58, pp. 649-662, (May 23, 2002).
"FRAC Code List 2: Fungicides sorted by modes of action," FRAC Fungicide Resistance Action Committee, pp. 1-10, (Jan. 1, 2006) XP 007914432.

(Continued)

*Primary Examiner* — John Pak
(74) *Attorney, Agent, or Firm* — Oblon, McClelland, Maier & Neustadt, L.L.P.

(57) ABSTRACT

To provide a fungicidal composition having stable and high fungicidal effects against cultivated crops infected with plant diseases resulting from plant diseases.
A fungicidal composition containing, as active ingredients, (a) a benzoylpyridine derivative represented by the formula (I) or its salt:

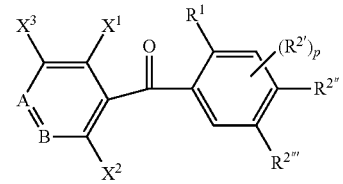

wherein when A is —N═, B is —CX$^4$═; when A is —CH═, B is —N═; each of X$^1$ and X$^2$ which are independent of each other, is a halogen atom, an alkoxy group, a hydroxyl group, an alkyl group, a CF$_3$ group or an alkylthio group; X$^3$ is a hydrogen atom, a halogen atom, an alkoxy group, an alkyl group, a CF$_3$ group or an alkylthio group; X$^4$ is a hydrogen atom, a halogen atom, an alkoxy group, an alkyl group, a CF$_3$ group or an alkylthio group; R$^1$ is an alkyl group; R$^{2'}$ is an alkoxy group; p is 0, 1 or 2; and each of R$^{2''}$ and R$^{2'''}$ is an alkoxy group, and (b) at least one additional fungicide.

18 Claims, No Drawings

(56) References Cited

OTHER PUBLICATIONS

"QoI working group of FRAC Minutes of the meeting," FRAC Fungicide Resistance Action Committee, pp. 1-11, (2007), XP 007914428.
"Guanidines," Guanidines Overview, pp. 1199-1210, (Jan. 1, 1999) XP 002596964.
International Search Report dated Sep. 7, 2010 in PCT/JP09/062259 filed Jun. 30. 2009.
Japanese Office Action dated Oct. 8, 2013, in Japan Patent Application No. 2009-155522 (with English translation).
K. Gopinath, et al. "Effect of propiconazole and difenoconazole on the control of anthracnose of chilli fruits caused by Colletotrichum capsici" Crop Protection, vol. 25, pp. 1024-1031, 2006.

\* cited by examiner

FUNGICIDAL COMPOSITION AND METHOD FOR CONTROLLING PLANT DISEASES

This application is a Divisional of U.S. application Ser. No. 14/572,237, filed on Dec. 16, 2014, allowed, which is a Divisional of U.S. application Ser. No. 13/002,361, filed on Jan. 3, 2011, now U.S. Pat. No. 8,962,661, which is a National Stage of International Application No. PCT/JP2009/062259, filed on Jun. 30, 2009, which claims priority to Japanese application Nos. 2008-174963, filed on Jul. 3, 2008, and 2008-292511, filed on Nov. 14, 2008.

TECHNICAL FIELD

The present invention relates to a fungicidal composition useful as an agricultural and horticultural fungicide having remarkably improved preventive and/or curative effects against plant diseases, and a method for controlling plant diseases by using such a composition.

BACKGROUND ART

Patent Document 1 discloses that a benzoylpyridine derivative which is an active ingredient of the fungicidal composition in the present invention is useful as a fungicide and may be used in combination with another fungicide as the case requires. Further, Patent Document 2 discloses that in combination with another fungicide, it is possible to obtain a fungicidal composition having a remarkably excellent synergic effect. However, it has not been known that the composition in the particular combination of the present invention has a remarkably excellent fungicidal effect.

Patent Document 1: WO02/02527
Patent Document 2: WO2005/041663

DISCLOSURE OF THE INVENTION

Problems that the Invention is to Solve

Each of benzoylpyridine derivatives represented by the formula (I) given hereinafter, may be inadequate in its controlling effect against a specific plant disease, its residual effect may last only a relatively short time, or its rainfastness may be weak, and thus, depending upon the application site, it may practically have only an inadequate controlling effect against plant diseases.

Means of Solving the Problems

The present inventors have conducted a research to solve the above problems and as a result, found that when a benzoylpyridine derivative represented by the formula (I) given hereinafter and a specific fungicide are used in combination, an unexpectedly excellent fungicidal effect can be obtained as compared with a case where the respective compounds are used alone. Thus, the present invention has been accomplished.

That is, the present invention relates to a fungicidal composition containing, as active ingredients, (a) a benzoylpyridine derivative represented by the formula (I) or its salt:

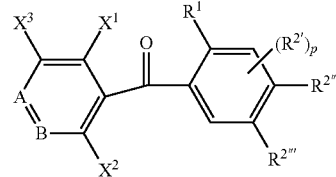

wherein when A is $-N=$, B is $-CX^4=$; when A is $-CH=$, B is $-N=$; each of $X^1$ and $X^2$ which are independent of each other, is a halogen atom, an alkoxy group, a hydroxyl group, an alkyl group, a $CF_3$ group or an alkylthio group; $X^3$ is a hydrogen atom, a halogen atom, an alkoxy group, an alkyl group, a $CF_3$ group or an alkylthio group; $X^4$ is a hydrogen atom, a halogen atom, an alkoxy group, an alkyl group, a $CF_3$ group or an alkylthio group; $R^1$ is an alkyl group; $R^{2'}$ is an alkoxy group; p is 0, 1 or 2; and each of $R^{2''}$ and $R^{2'''}$ is an alkoxy group, and (b) at least one fungicide selected from the group consisting of pyraclostrobin, boscalid, penthiopyrad, pyribencarb, meptyldinocap, difenoconazole, dodine, sulfur, flutianil, 6-t-butyl-8-fluoro-2,3-dimethylquinolin-4-yl acetate and a compound represented by the formula (II):

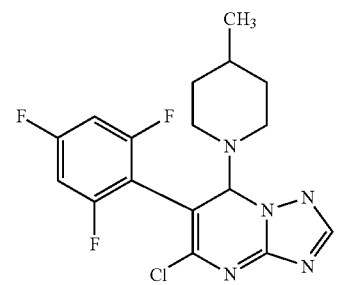 [SMILES: CC1CCN(C2C(c3c(F)cc(F)cc3F)=C(Cl)N=C3N=CNN32)CC1]

Further, the present invention relates to a method for controlling plant diseases, which comprises applying the above fungicidal composition to plants.

In the formula (I), the halogen atom is fluorine, chlorine, bromine or iodine, and it may, for example, be preferably fluorine, chlorine or bromine.

An alkyl moiety in the alkyl group, alkoxyl group and alkylthio group in the formula (I) is preferably $C_{1-6}$ alkyl (such as methyl, ethyl, propyl, isopropyl, butyl, isobutyl or t-butyl), and among them, $C_{1-4}$ alkyl is preferred.

The benzoylpyridine derivative represented by the formula (I) may form a salt together with an acidic substance, and it may form, for example, an inorganic acid salt such as a hydrochloride, a hydrobromide, a phosphate, a sulfate or a nitrate; or an organic acid salt such as an acetate, a benzoate, a p-toluenesulfonate, a methanesulfonate or a propanesulfonate.

The benzoylpyridine derivative represented by the formula (I) may be prepared by production processes as disclosed in Patent Documents 1 and 2. Further, it may be produced also by a method in accordance with Journal of Organic Chemistry, 58, 7832 (1993), and European Journal of Organic Chemistry, 7, 1371-1376 (2001).

As the fungicide (b) which is mixed with the benzoylpyridine derivative represented by the above formula (I) or its salt, at least one fungicide may be mentioned which is selected from the group consisting of Pyraclostrobin, Boscalid, Penthiopyrad, Pyribencarb, Meptyldinocap, Difenoconazole, Dodine, Sulfur, flutianil, 6-t-butyl-8-fluoro-2,3-dimethylquinolin-4-yl acetate and a compound represented by the formula (II):

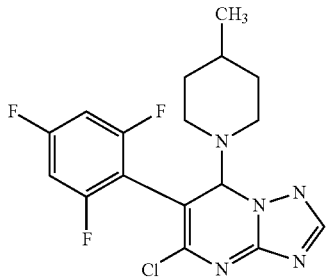 [SMILES: CC1CCN(C2C(c3c(F)cc(F)cc3F)=C(Cl)N=C3N=CNN32)CC1]

Pyraclostrobin as the fungicide (b) is a compound disclosed in The Pesticide Manual (14th edition; BRITISH CROP PROTECTION COUNCIL) p. 900-901. Boscalid is a compound disclosed in The Pesticide Manual (14th edition; BRITISH CROP PROTECTION COUNCIL), p. 110. Penthiopyrad is a compound disclosed in The Pesticide Manual (14th edition; BRITISH CROP PROTECTION COUNCIL), p. 811. Pyribencarb is a compound disclosed in AG CHEM NEW COMPOUND REVIEW VOLUME 25, 2007, p. 58. Meptyldinocap is a compound disclosed in The Pesticide Manual (14th edition; BRITISH CROP PROTECTION COUNCIL) p. 356-358. Difenoconazole is a compound disclosed in The Pesticide Manual (14th edition; BRITISH CROP PROTECTION COUNCIL) p. 323-325. Dodine is a compound disclosed in The Pesticide Manual (14th edition; BRITISH CROP PROTECTION COUNCIL) p. 381-382. Sulfur is a compound disclosed in The Pesticide Manual (14th edition; BRITISH CROP PROTECTION COUNCIL) p. 978-979. Flutianil is a compound which is provisionally registered as ISO 1750, and its CAS No. is 958647-10-4. 6-t-butyl-8-fluoro-2,3-dimethylquinolin-4-yl acetate is described in WO 98/55460, Table 1, as compound No. 84 and is a 4-quinolinol derivative. Further, the compound of the formula (II) is a compound disclosed in AG CHEM NEW COMPOUND REVIEW, VOLUME 25, 2007, page 14 as CAS No. 214706-53-3.

Effect of the Invention

The fungicidal compound of the present invention has stable and high fungicidal effects for cultivated crops infected with plant diseases, and it is possible to control the plant diseases by this composition.

BEST MODE FOR CARRYING OUT THE INVENTION

The compound represented by the above formula (I) may be a compound wherein A is —CH= and B is —N= i.e. a compound represented by the formula (I-1):

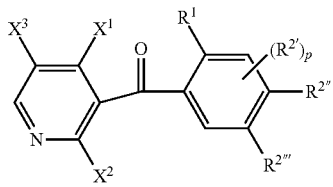

wherein $X^1$, $X^2$, $X^3$, $R^1$, $R^{2'}$, $R^{2''}$ and $R^{2'''}$ are as defined above, or a compound wherein A is —N= and B is —CX$^4$= i.e. a compound represented by the formula (I-2):

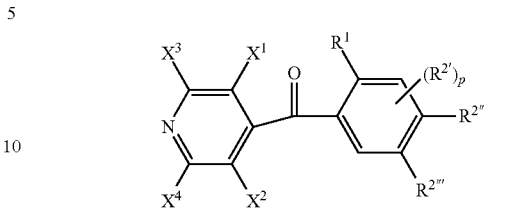

wherein $X^1$, $X^2$, $X^3$, $X^4$, $R^1$, $R^{2'}$, $R^{2''}$ and $R^{2'''}$ are as defined above.

Among compounds represented by the above formula (I-1), it is preferred to use at least one compound selected from the group consisting of 3-(2,3,4-trimethoxy-6-methylbenzoyl)-4-bromo-5-chloro-2-methoxypyridine (Compound No. 1), 3-(2,3,4-trimethoxy-6-methylbenzoyl)-5-chloro-4-ethyl-2-methoxypyridine (Compound No. 2), 3-(4,5-dimethoxy-2-methylbenzoyl)-4,5-dichloro-2-methoxypyridine (Compound No. 3), 3-(5-ethoxy-4-methoxy-2-methylbenzoyl)-4,5-dichloro-2-methoxypyridine (Compound No. 4), 3-(2,3,4-trimethoxy-6-methylbenzoyl)-4-bromo-5-chloro-2-ethoxypyridine (Compound No. 5), 3-(2,3,4-trimethoxy-6-methylbenzoyl)-5-chloro-2-ethoxy-4-methylpyridine (Compound No. 6), 3-(2,3,4-trimethoxy-6-methylbenzoyl)-5-bromo-4-chloro-2-ethoxypyridine (Compound No. 7), 3-(2,3,4-trimethoxy-6-methylbenzoyl)-4-chloro-5-iodo-2-methoxypyridine (Compound No. 8), 3-(2,3,4-trimethoxy-6-methylbenzoyl)-5-iodo-2,4-dimethoxypyridine (Compound No. 9), 3-(2,3,4-trimethoxy-6-methylbenzoyl)-5-chloro-2-methoxy-4-methylthiopyridine (Compound No. 10), 3-(2,3,4-trimethoxy-6-methylbenzoyl)-5-chloro-2,4-dimethoxypyridine (Compound No. 11), 3-(2,3,4-trimethoxy-6-methylbenzoyl)-4,5-dibromo-2-methoxypyridine (Compound No. 12), 3-(2,3,4-trimethoxy-6-methylbenzoyl)-4-bromo-2-methoxy-5-methylpyridine (Compound No. 13), 3-(2,3,4-trimethoxy-6-methylbenzoyl)-5-bromo-4-trifluoromethyl-2-methoxypyridine (Compound No. 14), 3-(2,3,4-trimethoxy-6-methylbenzoyl)-4,5-dichloro-2-methoxypyridine (Compound No. 15), 3-(2,3,4-trimethoxy-6-methylbenzoyl)-2,4-dichloro-5-methylpyridine (Compound No. 16), 3-(2,3,4-trimethoxy-6-methylbenzoyl)-2,4-dichloro-5-iodopyridine (Compound No. 17), 3-(2,3,4-trimethoxy-6-methylbenzoyl)-2-fluoro-4-iodo-5-methylpyridine (Compound No. 18), 3-(2,3,4-trimethoxy-6-methylbenzoyl)-2-fluoro-4,5-dimethylpyridine (Compound No. 19), 3-(2,3,4-trimethoxy-6-methylbenzoyl)-2-methoxy-4,5-dimethylpyridine (Compounds No. 20), 3-(2-ethoxy-3,4-dimethoxy-6-methylbenzoyl)-2-ethoxy-4,5-dimethylpyridine (Compound No. 21), 3-(2,3,4-trimethoxy-6-methylbenzoyl)-4,5-dimethyl-2-methylthiopyridine (Compound No. 22), 3-(2,3,4-trimethoxy-6-methylbenzoyl)-5-bromo-4-chloro-2-methoxypyridine (Compound No. 23), 3-(2,3,4-trimethoxy-6-methylbenzoyl)-4-chloro-2-methoxy-5-methylpyridine (Compound No. 24), 3-(2,3,4-trimethoxy-6-methylbenzoyl)-2-chloro-5-trifluoromethyl-4-methylpyridine (Compound No. 25), 3-(2,3,4-trimethoxy-6-methylbenzoyl)-5-trifluoromethyl-2-methoxy-4-methylpyridine (Compound No. 26), 3-(2,3,4-trimethoxy-6-methylbenzoyl)-2,4-dichloro-5-trifluoromethylpyridine (Compound No. 27), 3-(2,3,4-trimethoxy-6-methylbenzoyl)-4-chloro-5-trifluoromethyl-2-methoxypyridine (Compound No. 28), 3-(2,3,4-trimethoxy-6-methylbenzoyl)-5- chloro-4-ethynyl-2-methoxypyridine (Compound No. 29), 3-(2,3,4-trimethoxy-6-methylbenzoyl)-5-chloro-4-fluoromethyl-2-methoxypyridine (Compound No. 30), 3-(2,3,4-trimethoxy-6-methylbenzoyl)-5-bromo-4-fluoromethyl-2-methoxypyridine (Compound No. 31), 3-(2,3,4-trimethoxy-6-methylbenzoyl)-4-fluoromethyl-2-methoxy-5-methylpyridine (Compound No. 32), 3-(2,3,4-trimethoxy-6-methylbenzoyl)-5-chloro-4-difluoromethyl-2-methoxypyridine (Compound No. 33), 3-(2,3,4-trimethoxy-6-methylbenzoyl)-5-ethyl-4-trifluoromethyl-2-methoxypyridine (Compound No. 34), 3-(2,3,4-trimethoxy-6-methylbenzoyl)-5-chloro-2-methoxy-4-methylpyridine (Compound No. 35), 3-(2,3,4-trimethoxy-6-methylbenzoyl)-5-bromo-2-methoxy-4-methylpyridine (Compound No. 36), 3-(2,3,4-trimethoxy-6-methylbenzoyl)-4-trifluoromethyl-2-methoxy-5-methylpyridine (Compound No. 37) and 3-(4,5-dimethoxy-2-methylbenzoyl)-5-chloro-2-methoxy-4-methylpyridine (Compound No. 38). Among them, 3-(2,3,4-trimethoxy-6-methylbenzoyl)-5-chloro-2-methoxy-4-methylpyridine is most preferred.

Among compounds represented by the above formula (I-2), it is preferred to use at least one compound selected from the group consisting of 4-(2,3,4-trimethoxy-6-methylbenzoyl)-2,5-dichloro-3-trifluoromethylpyridine (Compound No. 39), 4-(2,3,4-trimethoxy-6-methylbenzoyl)-2-chloro-3-trifluoromethyl-5-methoxypyridine (Compound No. 40), 4-(2,3,4-trimethoxy-6-methylbenzoyl)-2-bromo-3-trifluoromethyl-5-methoxypyridine (Compound No. 41), 4-(2,3,4-trimethoxy-6-methylbenzoyl)-2,3,5-trichloropyridine (Compound No. 42), 4-(2,3,4-trimethoxy-6-methylbenzoyl)-3,5-dichloropyridine (Compound No. 43), 4-(2,3,4-trimethoxy-6-methylbenzoyl)-3-chloro-5-methoxypyridine (Compound No. 44), 4-(2,3,4-trimethoxy-6-methylbenzoyl)-2-bromo-3-chloro-5-methoxypyridine (Compound No. 45) and 4-(2,3,4-trimethoxy-6-methylbenzoyl)-3-bromo-5-methoxypyridine (Compound No. 46). Among them, it is most preferred to use at least one compound selected from the group consisting of 4-(2,3,4-trimethoxy-6-methylbenzoyl)-2,5-dichloro-3-trifluoromethylpyridine and 4-(2,3,4-trimethoxy-6-methylbenzoyl)-2-chloro-3-trifluoromethyl-5-methoxypyridine.

The fungicidal composition of the present invention is useful particularly as an agricultural and horticultural fungicide. As the agricultural and horticultural fungicide, it is effective for controlling diseases such as blast, brown spot or sheath blight of rice (*Oryza sativa*, etc.); powdery mildew, scab, rust, snow mold, snow blight, loose smut, eye spot, leaf spot or glume blotch of cereals (*Hordeum vulgare, Tricum aestivum*, etc.); melanose or scab of citrus (*Citrus* spp., etc.); blossom blight, powdery mildew, Alternaria leaf spot or scab of apple (*Malus pumila*); scab or black spot of pear (*Pyrus serotina Pyrus ussuriensis, Pyrus communis*); brown rot, scab or Phomopsis rot of peach (*Prunus persica*, etc.); anthracnose, ripe rot, powdery mildew or downy mildew of grape (*Vitis vinifera* spp., etc.); anthracnose or brown stem rot of Japanese persimmon (*Diospyros kaki*, etc.); anthracnose, powdery mildew, gummy stem blight or downy mildew of cucurbit (*Cucumis melo*, etc.); early blight, leaf mold or late blight of tomato (*Lycopersicon esculentum*); various Alternaria disease pathogens of cruciferous vegetables (*Brassica* sp., *Raphanus* sp., etc); late blight or early blight of potato (*Solanum tuberosum*); powdery mildew of strawberry (*Fraciaria*, etc.); and gray mold or disease caused by *Sclerotinia* of various crops. It is particularly effective against powdery mildew of cereals and vegetables and blast of rice. Further, it is effective also for controlling soil diseases caused by plant pathogens such as *Fusarium, Pythium, Rhizoctonia, Verticillium* and *Plasmodiophora*.

The plurality of the active ingredients constituting the fungicidal composition of the present invention are, in the same manner as conventional agricultural chemicals, mixed with various adjuvants and formulated into various formulations such as a dust, granules, water-dispersible granules, a wettable powder, a water-based suspension concentrate, an oil-based suspension concentrate, water soluble granules, an emulsifiable concentrate, a soluble concentrate, a paste, an aerosol and an ultra low-volume formulation. However, so long as the purpose of the present invention can be accomplished, any type of formulation which is commonly used in this field is applicable. Such adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethyl sulfoxide, dimethylformamide, dimethylacetamide, N-methyl-2-pyrrolidone and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected from known components so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed. The blend ratio of the active ingredient components to the various adjuvants is usually from 0.005:99.995 to 95:5, preferably from 0.2:99.8 to 90:10. In the actual application of such a formulation, it may be used as it is, or may be diluted to a predetermined concentration with a diluent such as water, and various spreaders may be added thereto, as the case requires.

A method for controlling plant diseases, which comprises applying the fungicidal composition of the present invention to agricultural and horticultural plants, is also included in the present invention. The concentration of the fungicidal composition of the present invention can not generally be defined, as it varies depending upon the crop plants to be treated, the application method, the type of the formulation, the dose, etc. However, it is applied in a concentration of the active ingredients being usually from 0.1 to 10,000 ppm, preferably from 1 to 2,000 ppm in the case of foliage treatment, and usually from 10 to 100,000 g/ha, preferably from 200 to 20,000 g/ha in the case of soil treatment.

The formulation containing the fungicidal composition of the present invention or a diluted product thereof may be applied by an application method which is commonly used, such as spreading (spreading, spraying, misting, atomizing, grain diffusing or application on water surface), soil application (such as mixing or irrigation) or surface application (such as coating, dust coating or covering). Further, it may be applied also by so-called ultra low volume. In this method, the formulation may contain 100% of the active ingredient.

In the fungicidal composition of the present invention, the appropriate mixing weight ratio of the benzoylpyridine derivative (a) represented by the formula (I) or its salt to another fungicide (b) is usually from 1:10,000 to 10,000:1, preferably from 1:1,000 to 1,000:1, more preferably from 1:200 to 200:1.

EXAMPLES

Now, the present invention will be described in further detail with reference to Examples. However, it should be understood that the present invention is by no means restricted thereto.

Test Example 1: Test on Preventive Effect Against Wheat Powdery Mildew

Wheat (cultivar: Norin-61-go) was cultivated in a plastic pot having a diameter of 7.5 cm, and when it reached 1.5-leaf stage, 10 ml of a chemical solution having each test compound adjusted to a prescribed concentration, was applied by a spray gun in an amount of 1000 L/ha. After the chemical solution dried, conidia of *Erysiphe graminis* were dusted and inoculated and maintained in a constant temperature chamber at 20° C. From 6 to 8 days after the inoculation, the area of sporulation was investigated, and the disease rate was determined in accordance with the following formula, and the results are shown in Tables 1 to 4. The average lesion area in the non-treated plot was determined in the same manner as for the treated plot except that water was applied by a spray gun instead of the chemical solution.

Disease rate=(a/b)×100 a: average lesion area in the treated plot
b: average lesion area in the non-treated plot Theoretical values were calculated in accordance with the Colby's formula. The fungicidal composition of the present invention has a synergistic effect regarding the test on preventive effect against wheat powdery mildew, when the experimental value is lower than the theoretical value. Theoretical values by the Colby's formula in such cases are shown in brackets in Tables 1 to 4.

TABLE 1

| Concentration of | Concentration of compound No. 35 | | |
|---|---|---|---|
| Pyraclostrobin | 1.6 ppm | 0.8 ppm | 0 ppm |
| 400 ppm | 7.5 (70) | 30 (70) | 100 |
| 200 ppm | 10 (70) | 50 (70) | 100 |

TABLE 1-continued

| Concentration of | Concentration of compound No. 35 | | |
|---|---|---|---|
| Pyraclostrobin | 1.6 ppm | 0.8 ppm | 0 ppm |
| 100 ppm | 30 (70) | 50 (70) | 100 |
| 0 ppm | 70 | 70 | 100 |

TABLE 2

| Concentration of | Concentration of compound No. 39 | | | |
|---|---|---|---|---|
| Pyraclostrobin | 6.3 ppm | 3.1 ppm | 1.6 ppm | 0 ppm |
| 400 ppm | 5 (60) | 10 (75) | 60 (85) | 100 |
| 200 ppm | 7.5 (60) | 50 (75) | 70 (85) | 100 |
| 100 ppm | 50 (60) | 60 (75) | 70 (85) | 100 |
| 0 ppm | 60 | 75 | 85 | 100 |

TABLE 3

| Concentration of | Concentration of compound No. 40 | |
|---|---|---|
| Pyraclostrobin | 0.8 ppm | 0 ppm |
| 400 ppm | 10 (50) | 100 |
| 200 ppm | 30 (50) | 100 |
| 0 ppm | 50 | 100 |

TABLE 4

| Concentration of | Concentration of compound No. 35 | | | | |
|---|---|---|---|---|---|
| Difenoconazole | 6.3 ppm | 3.1 ppm | 1.6 ppm | 0.8 ppm | 0 ppm |
| 50 ppm | 5 (24) | 10 (40) | 30 (40) | 30 (40) | 40 |
| 25 ppm | 5 (42) | 8 (70) | 50 (70) | 50 (70) | 70 |
| 12.5 ppm | 8 (51) | 50 (85) | 50 (85) | 60 (85) | 85 |
| 0 ppm | 60 | 100 | 100 | 100 | 98 |

Test Example 2: Test on Preventive Effect Against Cucumber Powdery Mildew

Cucumber (cultivar: Suyo) was cultivated in a plastic pot having a diameter of 7.5 cm, and when it reached 1.5-leaf stage, 10 ml of a chemical solution having the compound of the present invention adjusted to a prescribed concentration, was applied by a spray gun. After the chemical solution dried, a suspension of conidia of *Sphaerotheca cucurbitae* was sprayed and inoculated and maintained in a constant temperature chamber at 20° C. From 9 to 10 days after the inoculation, the area of sporulation was investigated, and the disease rate was determined in the same manner as in Test Example 1, and the results are shown in Tables 5 to 20. The average lesion area in the non-treated plot was determined in the same manner as for the treated plot except that water was applied by a spray gun instead of the chemical solution.

Further, theoretical values by the Colby's formula are shown in brackets in Tables 5 to 20.

TABLE 5

| Concentration of Pyribencarb | Concentration of compound No. 35 | | |
|---|---|---|---|
| | 6.3 ppm | 0.8 ppm | 0 ppm |
| 50 ppm | 5.4 (12.3) | 43.8 (58.4) | 63.2 |
| 25 ppm | 4.9 (12.3) | 48.7 (58.4) | 63.2 |
| 12.5 ppm | 2.9 (14.2) | 43.8 (67.5) | 73.0 |
| 0 ppm | 19.5 | 92.4 | 97.3 |

TABLE 6

| Concentration of Pyribencarb | Concentration of compound No. 39 | | |
|---|---|---|---|
| | 12.5 ppm | 6.3 ppm | 0 ppm |
| 50 ppm | 14.6 (36.9) | 24.3 (55.4) | 63.2 |
| 25 ppm | 19.5 (36.9) | 34.1 (55.4) | 63.2 |
| 12.5 ppm | 24.3 (42.6) | 29.2 (63.9) | 73.0 |
| 0 ppm | 58.4 | 87.6 | 97.3 |

TABLE 7

| Concentration of Pyribencarb | Concentration of compound No. 40 | |
|---|---|---|
| | 3.1 ppm | 0 ppm |
| 25 ppm | 14.6 (24.6) | 63.2 |
| 12.5 ppm | 19.5 (28.4) | 73.0 |
| 0 ppm | 38.9 | 97.3 |

TABLE 8

| Concentration of Boscalid | Concentration of compound No. 35 | | |
|---|---|---|---|
| | 3.1 ppm | 1.6 ppm | 0 ppm |
| 25 ppm | 0.4 (2.2) | 6.5 (12.2) | 25.8 |
| 12.5 ppm | 0.9 (3.7) | 8.6 (20.3) | 43.0 |
| 0 ppm | 8.6 | 47.3 | 86.0 |

TABLE 9

| Concentration of Boscalid | Concentration of compound No. 39 | | |
|---|---|---|---|
| | 12.5 ppm | 6.3 ppm | 0 ppm |
| 25 ppm | 4.3 (11.1) | 0 (13.3) | 25.8 |
| 12.5 ppm | 8.6 (18.5) | 21.5 (22.2) | 43.0 |
| 0 ppm | 43.0 | 51.6 | 86.0 |

TABLE 10

| Concentration of Boscalid | Concentration of compound No. 40 | | |
|---|---|---|---|
| | 3.1 ppm | 1.6 ppm | 0 ppm |
| 25 ppm | 0.4 (2.2) | 4.3 (11.1) | 25.8 |
| 12.5 ppm | 0 (3.7) | 12.9 (18.5) | 43.0 |
| 6.3 ppm | 2.6 (3.7) | 12.9 (18.5) | 43.0 |
| 0 ppm | 8.6 | 43.0 | 86.0 |

TABLE 11

| Concentration of Penthiopyrad | Concentration of compound No. 35 | | |
|---|---|---|---|
| | 3.1 ppm | 1.6 ppm | 0 ppm |
| 0.8 ppm | 0.4 (4.4) | 17.2 (24.4) | 51.6 |
| 0.4 ppm | 0.9 (6.7) | 30.1 (36.6) | 77.4 |
| 0 ppm | 8.6 | 47.3 | 86.0 |

TABLE 12

| Concentration of Penthiopyrad | Concentration of compound No. 39 | |
|---|---|---|
| | 6.3 ppm | 0 ppm |
| 1.6 ppm | 4.3 (8.9) | 17.2 |
| 0.8 ppm | 8.6 (26.6) | 51.6 |
| 0.4 ppm | 34.4 (39.9) | 77.4 |
| 0 ppm | 51.6 | 86.0 |

TABLE 13

| Concentration of Meptyldinocap | Concentration of compound No. 35 | |
|---|---|---|
| | 0.4 ppm | 0 ppm |
| 1.6 ppm | 25 (36) | 60 |
| 0.8 ppm | 30 (45) | 75 |
| 0 ppm | 60 | 100 |

TABLE 14

| Concentration of Meptyldinocap | Concentration of compound No. 39 | |
|---|---|---|
| | 6.3 ppm | 0 ppm |
| 3.1 ppm | 20 (27) | 60 |
| 1.6 ppm | 15 (27) | 60 |
| 0 ppm | 45 | 100 |

TABLE 15

| Concentration of the compound of the formula (II) | Concentration of compound No. 35 | |
|---|---|---|
| | 3.1 ppm | 0 ppm |
| 1.6 ppm | 5.4 (17.3) | 58.7 |
| 0.8 ppm | 0.5 (25.9) | 88.1 |
| 0 ppm | 29.4 | 97.9 |

TABLE 16

| Concentration of the compound of the formula (II) | Concentration of compound No. 39 | |
|---|---|---|
| | 12.5 ppm | 0 ppm |
| 6.3 ppm | 2.2 (3.7) | 8.6 |
| 3.1 ppm | 4.7 (7.4) | 17.2 |
| 1.6 ppm | 21.5 (25.9) | 60.2 |
| 0 ppm | 43 | 86 |

TABLE 17

| Concentration of the compound of the formula (II) | Concentration of compound No. 40 | |
|---|---|---|
| | 3.1 ppm | 0 ppm |
| 6.3 ppm | 0 (0.74) | 8.6 |
| 3.1 ppm | 0 (1.5) | 17.2 |
| 1.6 ppm | 4.3 (5.2) | 60.2 |
| 0 ppm | 8.6 | 86 |

TABLE 18

| Concentration of sulfur | Concentration of compound No. 35 | | | |
|---|---|---|---|---|
| | 3.1 ppm | 1.6 ppm | 0.8 ppm | 0 ppm |
| 25 ppm | 39.2 (60.5) | 44.1 (67.2) | 44.1 (67.2) | 68.6 |
| 12.5 ppm | 29.4 (77.8) | 49.0 (86.4) | 58.8 (86.4) | 88.2 |
| 6.3 ppm | 29.4 (86.4) | 53.9 (96.0) | 88.2 (96.0) | 98.0 |
| 0 ppm | 88.2 | 98.0 | 98.0 | 98.0 |

TABLE 19

| Concentration of flutianil | Concentration of compound No. 35 | | |
|---|---|---|---|
| | 6.3 ppm | 3.1 ppm | 0 ppm |
| 0.025 ppm | 0 (4.9) | 12.5 (52.0) | 65 |
| 0.0125 ppm | 3 (6.4) | 40 (68.0) | 85 |
| 0.0063 ppm | 3 (7.1) | 60 (76.0) | 95 |
| 0 ppm | 7.5 | 80 | 98.3 |

TABLE 20

| Concentration of 6-t-butyl-8-fluoro-2,3-dimethylquinolin-4-yl acetate | Concentration of compound No. 35 | | | | |
|---|---|---|---|---|---|
| | 3.1 ppm | 1.6 ppm | 0.8 ppm | 0.4 ppm | 0 ppm |
| 50 ppm | 7.4 (20.3) | 14.7 (33.8) | 29.5 (33.8) | 14.7 (33.8) | 34.4 |
| 25 ppm | 7.4 (34.8) | 34.4 (58.0) | 19.7 (58.0) | 24.6 (58.0) | 59.0 |
| 12.5 ppm | 7.4 (37.7) | 29.5 (62.8) | 39.3 (62.8) | 44.2 (62.8) | 63.9 |
| 6.3 ppm | 29.5 (49.3) | 49.2 (82.1) | 68.8 (82.1) | 68.8 (82.1) | 83.6 |
| 0 ppm | 59.0 | 98.3 | 98.3 | 98.3 | 98.3 |

Now, Formulation Examples of the present invention will be described below. However, the blend ratio, type of formulation or the like of the present invention is by no means restricted to the following Examples.

Formulation Example 1

| (a) Kaolin | 78 parts by weight |
|---|---|
| (b) Condensate of β-naphthalenesulfonic acid sodium salt with formalin | 2 parts by weight |
| (c) Polyoxyethylene alkylaryl sulfate | 5 parts by weight |
| (d) Hydrated amorphous silicon dioxide | 15 parts by weight |

A mixture of the above components, the compound of the formula (I) and Pyraclostrobin are mixed in a weight ratio of 8:1:1 to obtain a wettable powder.

Formulation Example 2

| (a) Compound of the formula (I) | 0.5 part by weight |
|---|---|
| (b) Pyraclostrobin | 0.5 part by weight |
| (c) Bentonite | 20 parts by weight |
| (d) Kaolin | 74 parts by weight |
| (e) Sodium lignin sulfonate | 5 parts by weight |

An appropriate amount of water for granulation is added to the above components and mixed, and the mixture is granulated to obtain granules.

Formulation Example 3

| (a) Compound of the formula (I) | 2 parts by weight |
|---|---|
| (b) Pyraclostrobin | 3 parts by weight |
| (c) Talc | 95 parts by weight |

The above components are uniformly mixed to obtain a dust.

The invention claimed is:

1. A fungicidal composition comprising, as active ingredients:
   (a) a benzoylpyridine derivative represented by the formula (I) or a salt thereof:

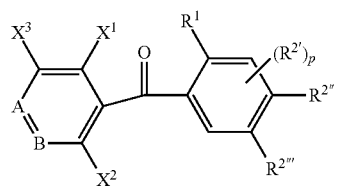

wherein
A is —N═ or —CH═;
when A is —N═, B is —CX$^4$═; when A is —CH═, B is —N═;
each of X$^1$ and X$^2$, which are independent of each other, is a halogen atom, an alkoxy group, a hydroxyl group, an alkyl group, a CF$_3$ group or an alkylthio group;
X$^3$ is a hydrogen atom, a halogen atom, an alkoxy group, an alkyl group, a CF$_3$ group or an alkylthio group;
X$^4$ is a hydrogen atom, a halogen atom, an alkoxy group, an alkyl group, a CF$_3$ group or an alkylthio group;

R¹ is an alkyl group;
R²' is an alkoxy group;
p is 0, 1 or 2; and
each of R²'' and R²''' is an alkoxy group, and
(b) at least one fungicide selected from the group consisting of boscalid, penthiopyrad, meptyldinocap, sulfur, flutianil, 6-t-butyl-8-fluoro-2,3-dimethylquinolin-4-yl acetate and a compound represented by the formula (II):

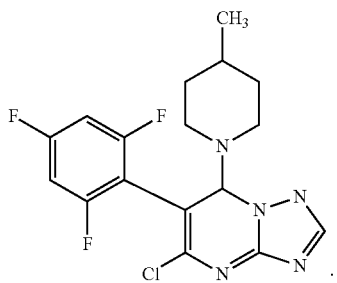 [SMILES: CC1CCN(C2C(c3c(F)cc(F)cc3F)=C(Cl)N=C3N=CNN32)CC1]

2. The fungicidal composition according to claim 1, wherein the fungicide (b) is at least one member selected from the group consisting of boscalid, penthiopyrad, meptyldinocap, sulfur and a compound represented by the formula (II):

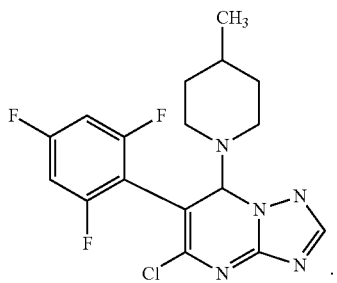 [SMILES: CC1CCN(C2C(c3c(F)cc(F)cc3F)=C(Cl)N=C3N=CNN32)CC1]

3. The fungicidal composition according to claim 1, wherein the fungicide (b) is at least one member selected from the group consisting of boscalid, penthiopyrad, meptyldinocap, sulfur and a compound represented by the formula (II):

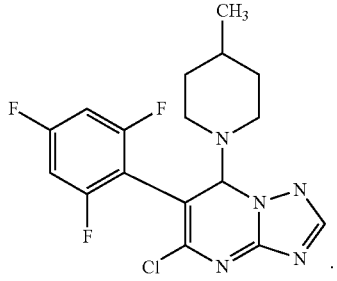 [SMILES: CC1CCN(C2C(c3c(F)cc(F)cc3F)=C(Cl)N=C3N=CNN32)CC1]

4. The fungicidal composition according to claim 1, wherein the benzoylpyridine derivative is a compound represented by the formula (I-1):

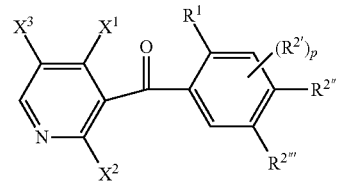

wherein
each of X¹ and X², which are independent of each other, is a halogen atom, an alkoxy group, a hydroxyl group, an alkyl group, a CF₃ group or an alkylthio group;
X³ is a hydrogen atom, a halogen atom, an alkoxy group, an alkyl group, a CF₃ group or an alkylthio group;
R¹ is an alkyl group;
R²' is an alkoxy group;
p is 0, 1 or 2; and
each of R²'' and R²''' is an alkoxy group.

5. The fungicidal composition according to claim 4, wherein the benzoylpyricline derivative is at least one member selected from the group consisting of 3-(2,3,4-trimethoxy-6-methylbenzoyl)-4-bromo-5-chloro-2-methoxypyridine, 3-(2,3,4-trimethoxy-6-methylbenzoyl)-5-chloro-4-ethyl-2-methoxypyridine, 3-(4,5-dimethoxy-2-methylbenzoyl)-4,5-dichloro-2-methoxypyridine, 3-(5-ethoxy-4-methoxy-2-methylbenzoyl)-4,5-dichloro-2-methoxypyridine, 3-(2,3,4-trimethoxy-6-methylbenzoyl)-4-bromo-5-chloro-2-ethoxypyridine, 3-(2,3,4-trimethoxy-6-methylbenzoyl)-5-chloro-2-ethoxy-4-methylpyridine, 3-(2,3,4-trimethoxy-6-methylbenzoyl)-5-bromo-4-chloro-2-ethoxypyridine, 3-(2,3,4-trimethoxy-6-methylbenzoyl)-4-chloro-5-iodo-2-methoxypyridine, 3-(2,3,4-trimethoxy-6-methylbenzoyl)-5-iodo-2,4-dimethoxypyridine, 3-(2,3,4-trimethoxy-6-methylbenzoyl)-5-chloro-2-methoxy-4-methylthiopyridine, 3-(2,3,4-trimethoxy-6-methylbenzoyl)-5-chloro-2,4-dimethoxypyridine, 3-(2,3,4-trimethoxy-6-methylbenzoyl)-4,5-dibromo-2-methoxypyridine, 3-(2,3,4-trimethoxy-6-methylbenzoyl)-4-bromo-2-methoxy-5-methylpyridine, 3-(2,3,4-trimethoxy-6-methylbenzoyl)-5-bromo-4-trifluoromethyl-2-methoxypyridine, 3-(2,3,4-trimethoxy-6-methylbenzoyl)-4,5-dichloro-2-methoxypyridine, 3-(2,3,4-trimethoxy-6-methylbenzoyl)-2,4-dichloro-5-methylpyridine, 3-(2,3,4-trimethoxy-6-methylbenzoyl)-2,4-dichloro-5-iodopyridine, 3-(2,3,4-trimethoxy-6-methylbenzoyl)-2-fluoro-4-iodo-5-methylpyridine, 3-(2,3,4-trimethoxy-6-methylbenzoyl)-2-fluoro-4,5-dimethylpyridine, 3-(2,3,4-trimethoxy-6-methylbenzoyl)-2-methoxy-4,5-dimethylpyridine, 3-(2-ethoxy-3,4-dimethoxy-6-methylbenzoyl)-2-ethoxy-4,5-dimethylpyridine, 3-(2,3,4-trimethoxy-6-methylbenzoyl)-4,5-dimethyl-2-methylthiopyridine, 3-(2,3,4-trimethoxy-6-methylbenzoyl)-5-bromo-4-chloro-2-methoxypyridine, 3-(2,3,4-trimethoxy-6-methylbenzoyl)-4-chloromethoxy-5-methylpyridine, 3-(2,3,4-trimethoxy-6-methylbenzoyl)-2-chloro-5-trifluoromethyl-4-methylpyridine, 3-(2,3,4-trimethoxy-6-methylbenzoyl)-5-trifluoromethyl-2-methoxy-4-methylpyridine, 3-(2,3,4-trimethoxy-6-methylbenzoyl)-2,4-dichloro-5-trifluoromethylpyridine, 3-(2,3,4-trimethoxy-6-methylbenzoyl)-4-chloro-5-trifluoromethyl-2-methoxypyridine, 3-(2,3,4-trimethoxy-6-methylbenzoyl)-5-chloro-4-ethinyl-2-methoxypyridine, 3-(2,3,4-trimethoxy-6-methylbenzoyl)-5-chloro-4-fluoromethyl-2-methoxypyridine, 3-(2,3,4-trimethoxy-6-methylbenzoyl)-5-bromo-4-fluoromethyl-2-methoxypyridine, 3-(2,3,4-trimethoxy-6-methylbenzoyl)-4-fluoromethyl-2-methoxy- 5-methylpyridine, 3-(2,3,4-trimethoxy-6-methylbenzoyl)-5-chloro-4-difluoromethyl-2-methoxypyridine, 3-(2,3,4-trimethoxy-6-methylbenzoyl)-5-ethyl-4-trifluoromethyl-2-methoxypyridine, 3-(2,3,4-trimethoxy-6-methylbenzoyl)-5-chloro-2-methoxy-4-methylpyridine, 3-(2,3,4-trimethoxy-6-methylbenzoyl)-5-bromo-2-methoxy-4-methylpyridine, 3-(2,3,4-trimethoxy-6-methylbenzoyl)-4-trifluoromethyl-2-methoxy-5-methylpyridine and 3-(4,5-dimethoxy-2-methyl-benzoyl)-5-chloro-2-methoxy-4-methylpyridine.

6. The fungicidal composition according to claim 1, wherein the benzoylpyridine derivative is a compound represented by the formula (I-2):

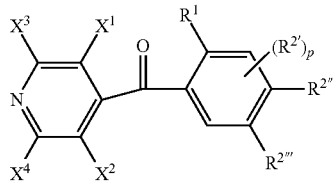

wherein
each of $X^1$ and $X^2$, which are independent of each other, is a halogen atom, an alkoxy group, a hydroxyl group, an alkyl group, a $CF_3$ group or an alkylthio group;
$X^3$ is a hydrogen atom, a halogen atom, an alkoxy group, an alkyl group, a $CF_3$ group or an alkylthio group;
$X^4$ is a hydrogen atom, a halogen atom, an alkoxy group, an alkyl group, a $CF_3$ group or an alkylthio group;
$R^1$ is an alkyl group;
$R^{2'}$ is an alkoxy group;
p is 0, 1 or 2; and
each of $R^{2''}$ and $R^{2'''}$ is an alkoxy group.

7. The fungicidal composition according to claim 6, wherein the benzoylpyridine derivative is at least one compound selected from the group consisting of 4-(2,3,4-trimethoxy-6-methylbenzoyl)-2,5-dichloro-3-trifluoromethylpyridine, 4-(2,3,4-trimethoxy-6-methylbenzoyl)-2-chloro-3-trifluoromethyl-5-methoxypyridine, 4-(2,3,4-trimethoxy-6-methylbenzoyl)-2-bromo-3-trifluoromethyl-5-methoxypyridine, 4-(2,3,4-trimethoxy-6-methylbenzoyl)-2,3,5-trichloropyridine, 4-(2,3,4-trimethoxy-6-methylbenzoyl)-3,5-dichloropyridine, 4-(2,3,4-trimethoxy-6-methylbenzoyl)-3-chloro-5-methoxypyridine, 4-(2,3,4-trimethoxy-6-methylbenzoyl)-2-bromo-3-chloro-5-methoxypyridine and 4-(2,3,4-trimethoxy-6-methylbenzoyl)-3-bromo-5-methylpyridine).

8. The fungicidal composition according to claim 1, wherein the benzoylpyridine derivative is at least one compound selected from the group consisting of 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-trifluoromethylpyridine and 4-(2,3,4-trimethoxy-6-methylbenzoyl)-2-chloro-3-trifluoromethyl-5-methoxypyridine.

9. The fungicidal composition according to claim 8, wherein the benzoylpyridine derivative is 3-(2,3,4-trimethoxy-6-methylbenzoyl)-5-chloro-2-methoxy-4-methylpyridine.

10. The fungicidal composition according to claim 8, wherein the benzoylpyridine derivative is at least one compound selected from the group consisting of 4-(2,3,4-trimethoxy-6-methylbenzoyl)-2,5-dichloro-3-trifluoromethylpyridine and 4-(2,3,4-trimethoxy-6-methylbenzoyl)-2-chloro-3-trifluoromethyl-5-methoxypyridine.

11. The fungicidal composition according to claim 1, wherein the mixing weight ratio of the benzoylpyridine derivative or a salt thereof (a) to the fungicide (b) is from 1:200 to 200:1.

12. The fungicidal composition according to claim 1, wherein (b) is boscalid.

13. The fungicidal composition according to claim 1, wherein (b) is penthiopyrad.

14. The fungicidal composition according to claim 1, wherein (b) is meptyldinocap.

15. The fungicidal composition according to claim 1, wherein (b) is sulfur.

16. The fungicidal composition according to claim 1, wherein (b) is 6-t-butyl-8-fluoro-2,3-dimethylquinolin-4-yl acetate.

17. The fungicidal composition according to claim 1, wherein (b) is a compound represented by the formula (II).

18. A method for controlling plant diseases, which comprises applying the fungicidal composition as defined in claim 1 to plants.

* * * * *